(12) United States Patent
 Takahashi et al.

(10) Patent No.: US 9,932,296 B2
(45) Date of Patent: *Apr. 3, 2018

(54) METHOD OF PRODUCING CYCLOALKANONE OXIME

(71) Applicant: Toray Industries, Inc., Tokyo (JP)

(72) Inventors: Toru Takahashi, Otsu (JP); Yasuyoshi Nishikawa, Nagoya (JP); Shoji Morita, Nagoya (JP)

(73) Assignee: Toray Industries, Inc. (JP)

( * ) Notice: Subject to any disclaimer, the term of this patent is extended or adjusted under 35 U.S.C. 154(b) by 55 days.

This patent is subject to a terminal disclaimer.

(21) Appl. No.: 14/409,299

(22) PCT Filed: Mar. 29, 2013

(86) PCT No.: PCT/JP2013/002168
§ 371 (c)(1),
(2) Date: Dec. 18, 2014

(87) PCT Pub. No.: WO2014/002340
PCT Pub. Date: Jan. 3, 2014

(65) Prior Publication Data
US 2015/0175531 A1   Jun. 25, 2015

(30) Foreign Application Priority Data
Jun. 27, 2012  (JP) .................................. 2012-144272

(51) Int. Cl.
*B01J 19/12* (2006.01)
*C07C 249/06* (2006.01)

(52) U.S. Cl.
CPC ........... *C07C 249/06* (2013.01); *B01J 19/122* (2013.01); *B01J 2219/1203* (2013.01)

(58) Field of Classification Search
CPC .. C07C 249/06; C07C 2101/14; B01J 19/127; B01J 19/122; B01J 2219/1203
(Continued)

(56) References Cited

U.S. PATENT DOCUMENTS 3,177,133 A * 4/1965 Horst Metzger et al. ......................... 204/157.83
3,320,143 A   5/1967 Baumgartner et al.
(Continued)

FOREIGN PATENT DOCUMENTS

GB     1095916 A  * 12/1967
JP     5-301858       11/1993
(Continued)

OTHER PUBLICATIONS

Journal of the Japan Petroleum Institute, vol. 17, No. 10, 1974, pp. 72-76 with partial English translation.
(Continued)

*Primary Examiner* — Ibrahime A Abraham
*Assistant Examiner* — Colleen M Raphael
(74) *Attorney, Agent, or Firm* — DLA Piper LLP (US)

(57) ABSTRACT

A method of producing a cycloalkanone oxime by a photochemical reaction of a cycloalkane with a photo nitrosating agent in a liquid by light irradiation includes irradiating the liquid with a light source configured to emit light satisfying conditions that, in an emission energy distribution with respect to wavelength of light, a wavelength providing a maximum value of emission energy is 550 nm to 700 nm and a continuous wavelength range including the wavelength providing the maximum value and outputting energy of or over 5% of the maximum value is equal to or less than 150 nm, wherein a ratio $\eta E/V$ of a light irradiation energy $\eta E$ out of electric power E input into the light source to a reaction volume V which is a volume of a space for the photochemi-
(Continued)

cal reaction of the cycloalkane with the photo nitrosating agent is equal to or greater than 5.5 w/L.

4 Claims, 2 Drawing Sheets

(58) Field of Classification Search
 USPC .................................. 204/157.83, 157.64
 See application file for complete search history.

(56) References Cited

U.S. PATENT DOCUMENTS

| | | | |
|---|---|---|---|
| 3,553,091 A * | 1/1971 | Nako Keiji et al. | 204/157.83 |
| 3,635,807 A * | 1/1972 | Guarino et al. | 204/157.83 |
| 3,717,561 A * | 2/1973 | Rigdon | B01J 19/122 |
| | | | 204/157.83 |
| 3,816,285 A * | 6/1974 | Osborn et al. | 204/157.83 |
| 6,197,999 B1 | 3/2001 | Ollivier et al. | |
| 2011/0137027 A1 | 6/2011 | Aubert | |
| 2014/0158522 A1 | 6/2014 | Takahashi et al. | |

FOREIGN PATENT DOCUMENTS

| | | |
|---|---|---|
| JP | 11-265687 A | 9/1999 |
| JP | 2010-006775 A | 1/2010 |
| JP | 2010-006776 A | 1/2010 |
| JP | 2011-521004 A | 7/2011 |
| JP | 2012-149055 A | 8/2012 |

OTHER PUBLICATIONS

"Kagaku Jiten," Dictionary of Chemistry, Tokyo Kagaku Dojin, 1994, pp. 457-458 with partial English translation.

* cited by examiner

METHOD OF PRODUCING CYCLOALKANONE OXIME

TECHNICAL FIELD

This disclosure relates to a method of producing a cycloalkanone oxime by a photonitrosation method.

BACKGROUND

Photoreactions indicate the general chemical reactions that lead to absorption of energy into molecules (i.e., radical reactant) by light irradiation to excite the molecules to a higher energy level (i.e., to the excited state) and initiate a reaction with the excited molecules. Photoreaction is also called photochemical reaction. According to "Kagaku Jiten," pages 457-458, Tokyo Kagaku Dojin, photoreactions include oxidation and reduction reactions with light and substitution and addition reactions with light. It is known that photoreactions have a variety of applications including not only photographic industries, photocopying technology, induction of photovoltaic power, but syntheses of organic compounds. Photochemical smog is also one type of photochemical reaction or more specifically unintentional photochemical reaction.

As described in JP 2010-6775 A and Journal of the Japan Petroleum Institute, Vol. 17, No. 10 (1974), pages 72-76, there is a known technique of synthesizing cyclohexanone oxime by the photochemical reaction. It is also known that the wavelength of 400 to 760 nm is desirable as the effective wavelength for the reactions of a cycloalkanone oxime. Examples of the light emitter having the energy output characteristics specialized in such a specific wavelength range include light sources such as light emitting diodes, lasers and organic electroluminescence (organic EL).

Light emitting diodes have the advantage of directly converting electrical energy into light by using a semiconductor. Light emitting diodes have drawn attention because of, for example, the less heat generation, efficient use of energy and the long life. In the recent years, LEDs of high efficiency and high output have been developed. As a result, this allows for replacement of incandescent lamps and fluorescent lamps with LEDs in general lighting use. In industrial use, LEDs are expected to achieve a practical level in some years.

In such environments, a production method of a cycloalkanone oxime having the following characteristics has been proposed in JP '775: (i) in the emission energy distribution with respect to the wavelength of the light source, it is desirable that the emission energy in the wavelength range of less than the wavelength of 400 nm is equal to or less than 5% of the maximum value of emission energy and that the emission energy in the wavelength range of greater than the wavelength of 760 nm is equal to or less than 5% of the maximum value of emission energy; (ii) the light emitting diodes used are those having the energy conversion efficiency equal to or greater than 3%; and (iii) a plurality of light emitting diodes arrayed in a plane along the side face of a photochemical reactor containing a photoreaction liquid are used to irradiate the photochemical liquid with light via the permeable photochemical reactor.

Additionally, the technique disclosed in JP 2010-6776 A synthesizes cyclohexanone oxime under the following conditions. Light emitting diodes are used as the light source. In the emission energy distribution with respect to the wavelength of the light source, a wavelength providing a maximum value of emission energy is 400 nm to 760 nm. A cooling jacket is provided on the rear surface of the light source, and a cooling medium is continuously introduced into the cooling jacket to forcibly and indirectly cool down the light source. In the emission energy distribution with respect to the wavelength of the light source, the wavelength providing the maximum value of emission energy is 430 nm to 650 nm. The integrated value of emission energy in the wavelength range of 400 nm to 760 nm relative to the emission energy in the wavelength range of 300 nm to 830 nm is equal to or greater than 95%. JP '776 also includes the descriptions on the temperature of the cooling medium introduced into the cooling jacket, the method of arraying the light emitting diodes, and the minimum distance of irradiation between the light emitting diodes and the side face of the photochemical reactor.

Furthermore, the technique disclosed in JP 2011-521004 A performs photonitrosation of a cycloalkanone oxime in a very narrow space with a microreactor using light emitting diodes.

Selectivity in the methods described in the above publications, i.e., a production ratio of a target component to a "raw material converted by the reaction," is not clearly specified. In the phase of industrialization, there is a need to improve the selectivity, i.e., setting the conditions to obtain a target product more efficiently.

It could therefore be helpful to maximize selectivity to reduce the amount of a raw material used in the phase of industrialization, while maintaining the production amount of a reaction product per input amount of electric power in the photonitrosation method using a light source having a narrow wavelength distribution.

SUMMARY

We provide a method of producing a cycloalkanone oxime by a photochemical reaction of a cycloalkane with a photo nitrosating agent in a liquid by light irradiation including irradiating the liquid with a light source configured to emit light satisfying conditions that, in an emission energy distribution with respect to wavelength of light, a wavelength providing a maximum value of emission energy is 550 nm to 700 nm and a continuous wavelength range including the wavelength providing the maximum value and outputting energy of or over 5% of the maximum value is equal to or less than 150 nm, wherein a ration $\eta E/V$ of a light irradiation energy $\eta E$ out of electric power E input into the light source to a reaction volume V which is a volume of a space for the photochemical reaction of the cycloalkane with the photo nitrosating agent is equal to or greater than 5.5 w/L.

We also provide the method of producing a cycloalkanone oxime by a photochemical reaction of a cycloalkane with a photo nitrosating agent in a liquid by light irradiation including irradiating the liquid with a light source configured to emit light satisfying conditions that, in an emission energy distribution with respect to wavelength of light, a wavelength providing a maximum value of emission energy is 550 nm to 700 nm and a continuous wavelength range including the wavelength providing the maximum value and outputting energy of or over 5% of the maximum value is equal to or less than 150 nm, wherein a ration $\eta E/V$ of a light irradiation energy $\eta E$ out of electric power E input into the light source to a reaction volume V which is a volume of a space for the photochemical reaction of the cycloalkane with the photo nitrosating agent is equal to or greater than 5.5 w/L, wherein the light source is a light emitting diode.

We also provide the method of producing a cycloalkanone oxime by a photochemical reaction of a cycloalkane with a photo nitrosating agent in a liquid by light irradiation including irradiating the liquid with a light source configured to emit light satisfying conditions that, in an emission energy distribution with respect to wavelength of light, a wavelength providing a maximum value of emission energy is 550 nm to 700 nm and a continuous wavelength range including the wavelength providing the maximum value and outputting energy of or over 5% of the maximum value is equal to or less than 150 nm, wherein a ration $\eta E/V$ of a light irradiation energy $\eta E$ out of electric power E input into the light source to a reaction volume V which is a volume of a space for the photochemical reaction of the cycloalkane with the photo nitrosating agent is equal to or greater than 5.5 w/L, wherein the wavelength providing the maximum value of emission energy is 600 nm to 650 nm.

We also provide the method of producing a cycloalkanone oxime by a photochemical reaction of a cycloalkane with a photo nitrosating agent in a liquid by light irradiation including irradiating the liquid with a light source configured to emit light satisfying conditions that, in an emission energy distribution with respect to wavelength of light, a wavelength providing a maximum value of emission energy is 550 nm to 700 nm and a continuous wavelength range including the wavelength providing the maximum value and outputting energy of or over 5% of the maximum value is equal to or less than 150 nm, wherein a ration $\eta E/V$ of a light irradiation energy $\eta E$ out of electric power E input into the light source to a reaction volume V which is a volume of a space for the photochemical reaction of the cycloalkane with the photo nitrosating agent is equal to or greater than 5.5 w/L, wherein the cycloalkane is cyclohexane, and the cycloalkanone oxime is cyclohexanone oxime.

We also provide a method of producing a lactam including reacting the cycloalkanone oxime produced by the method of producing a cycloalkanone oxime by a photochemical reaction of a cycloalkane with a photo nitrosating agent in a liquid by light irradiation including irradiating the liquid with a light source configured to emit light satisfying conditions that, in an emission energy distribution with respect to wavelength of light, a wavelength providing a maximum value of emission energy is 550 nm to 700 nm and a continuous wavelength range including the wavelength providing the maximum value and outputting energy of or over 5% of the maximum value is equal to or less than 150 nm, wherein a ration $\eta E/V$ of a light irradiation energy $\eta E$ out of electric power E input into the light source to a reaction volume V which is a volume of a space for the photochemical reaction of the cycloalkane with the photo nitrosating agent is equal to or greater than 5.5 w/L.

Our methods thus reduce impurity generation in the industrial level, and additionally saves electric power and energy and reduces the amount of a cycloalkane used as the raw material.

REFERENCE SIGNS LIST

1 Light emitting diode
2 Photochemical reactor
3 Heat sink
4 Cycloalkane supply line
5 Photo nitrosating agent supply line
6 Cooler
7 Reaction cooling water supply line
8 Reaction cooling water discharge line
9 Unreacted gas line
10 Reaction product line
11 Photochemical reactor (variable reaction volume type)
12 Circuit base for irradiation of light emitting diodes
13 Light emitting diode-exposure electrode substrate
14 light emitting diode (light emitting element)
15 Reactor input material circulation line
16 Reaction liquid circulation line
17 Reactor input material circulation line pump
18 Reaction liquid circulation line pump
21 Nitrosyl chloride injection line
22 Nitrosyl chloride-unreacted gas discharge line
23 Oily product extraction line
24 Separator
25 Raw material supply line

DETAILED DESCRIPTION

We found that controlling the ratio of the amount of light irradiation energy in a photoreaction to the amount of a reaction raw material present in a reaction field significantly improves selectivity while maintaining the production amount of a reaction product per input amount of electric power. This results in achieving selectivity at the level allowing for industrialization.

The reason for the significant improvement of the selectivity is attributed to the following. Controlling the ratio of the amount of light irradiation energy in the photoreaction to the amount of the reaction raw material present in the reaction field causes sufficient excitation of a photo nitrosating agent which absorbs photons under the condition of high photon density. This allows for a chemical reaction of a cycloalkane with the sufficiently dissociated photo nitrosating agent, thus increasing the yield of a cycloalkanone oxime as the target product while decreasing impurity generation. This results in significantly improving selectivity.

The ratio $\eta E/V$ of not less than 5.5 W/L is preferable, because of the following reason. The ratio $\eta E/V$ of less than 5.5 W/L fails to absorb a sufficient density of photons into the photo nitrosating agent and thereby causes insufficient excitation of the photo nitrosating agent, thus resulting in insufficient radical dissociation of the photo nitrosating agent. This leads to a chemical reaction of the cycloalkane with the insufficiently dissociated photo nitrosating agent and decreases the yield of the cycloalkane oxime as the target product while increasing impurity generation. This results in decreasing the selectivity. Accordingly, the ratio $\eta E/V$ is preferably equal to or greater than 5.5 W/L. The ratio ηE/V is also preferably equal to or less than 15.0 W/L and is more preferably equal to or less than 13.0 W/L.

The following describes examples of our methods with reference to the Drawings.

A light source used according to an example of our method is light emitting diodes. A light emitting diode is a semiconductor element configured to emit light by utilizing the electroluminescence (EL) effect. The light emitting diode emits light under application of a voltage in the forward direction. A light emitting diode is also referred to as LED. The following describes one example using light emitting diodes as the light source, but any other light source that satisfies the conditions of (1) described above such as laser or organic electroluminescence (organic EL), may be adopted for the light source.

Figure 1:
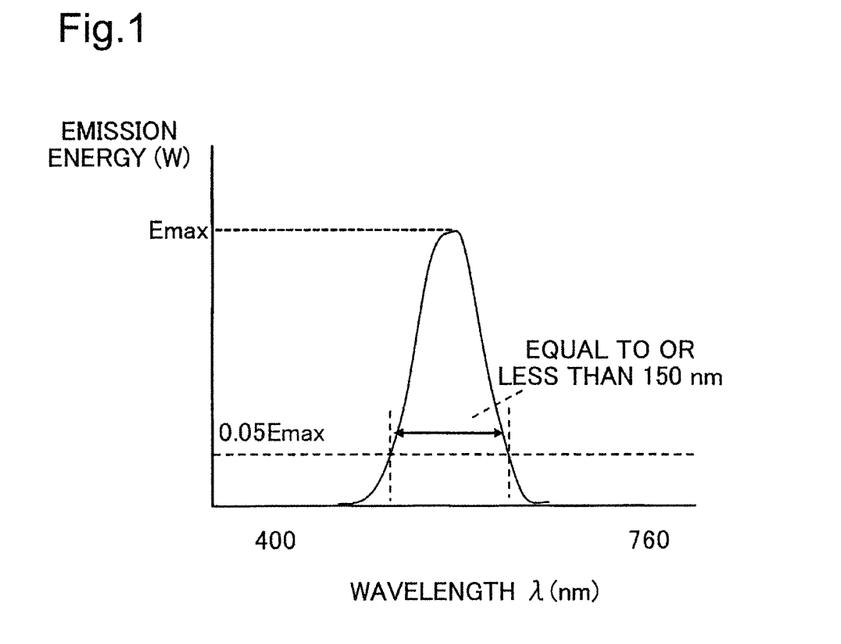
FIG. 1 is a graph showing an exemplary emission energy distribution of a light emitting diode used in one example having a maximum value of emission energy at a wavelength of about 615 nm.

A preferable example of emission energy distribution with respect to the wavelength of a light emitting diode used in one example is described with reference to FIG. 1. The "emission energy distribution" herein means a spectral distribution, for example, as shown in FIG. 1 with the wavelength as abscissa axis and the emission energy as ordinate axis. FIG. 1 is a graph showing one example of emission energy distribution of a light emitting diode having a maximum value of emission energy at a wavelength of about 615 nm. In FIG. 1, the unit of the ordinate axis is watt (W) and the unit of the abscissa axis is nanometer (nm).

The "maximum value of emission energy" according to this example means the highest value of emission energy in the emission energy distribution with respect to the wavelength measured in every 5 nm wavelength range. In the description below, the maximum value of emission energy is also called "peak intensity" and is expressed as Emax. A wavelength at which the emission energy reaches its maximum value is called "peak wavelength." The "peak wavelength" is a median value in a wavelength range providing the "peak intensity" in the emission energy distribution measured in every 5 nm wavelength range.

This example uses a light emitting diode configured to emit light satisfying the conditions that, in an emission energy distribution with respect to the wavelength, the peak wavelength is 550 nm to 700 nm and the width of a continuous wavelength range including the peak wavelength and outputting energy of or over 5% intensity of the peak intensity Emax is equal to or less than 150 nm (FIG. 1). The peak wavelength is more preferably 600 nm to 650 nm and is further more preferably 610 nm to 620 nm. In the emission energy distribution, the width of the continuous wavelength range including the peak wavelength and outputting the energy of or over 5% intensity of the peak intensity Emax is preferably equal to or less than 100 nm and is more preferably equal to or less than 50 nm.

Herein the "width of the continuous wavelength range outputting the energy of or over 5% intensity of the peak intensity Emax" is an interval between median values of wavelength ranges on both ends of one or more continuous wavelength ranges that have energy of or over 5% intensity of the peak intensity Emax in the emission energy distribution with respect to the wavelength measured in every 5 nm wavelength range. In the emission energy distribution with respect to the wavelength measured in every 5 nm wavelength range, however, when there is only one "continuous wavelength range including the peak wavelength and outputting the energy of or over 5% intensity of the peak intensity Emax," the "width of the continuous wavelength range outputting the energy of or over 5% intensity of the peak intensity Emax" is assumed to be 5 nm.

The reason why such emission energy distribution as described above is preferable is theoretically attributable to the following. Specifically, the photon energy required for radical dissociation of a nitrosating agent, for example, nitrosyl chloride, is obtained by the light having the wavelength equal to or less than 760 nm. In the emission energy distribution, substantially all photons have the wavelength equal to or less than 760 nm on conditions that (i) the wavelength range (width) including the peak wavelength that provides Emax and outputting the energy having the intensity of or over 5% of Emax is equal to or less than 50 to 100 nm and that (ii) the peak wavelength is equal to or less than 700 nm. As a result, this causes substantially all the energy to be in an effective wavelength range for radical dissociation. The irradiated light having the excessively small wavelength is likely to cause a side reaction. Accordingly, this example uses a light emitting diode that satisfies the condition that the peak wavelength providing the maximum value of emission energy is equal to or greater than 550 nm.

According to this example, the emission energy distribution and a photo-transformation efficiency η may be measured by the method described later. The emission energy distribution in an application using a plurality of light emitting diodes is obtained by measuring the emission energy distributions of the individual light emitting diodes used and subsequently summing up the measured emission energy distributions of all the light emitting diodes used. In this case, in the resulting emission energy distribution thus obtained, the wavelength providing the maximum value (Emax) of emission energy should be 550 nm to 700 nm. When the plurality of light emitting diodes used are light emitting diodes from one identical lot and are obviously expected to have the equal quality, a simplified method may be employed to measure the emission energy distribution of any arbitrary light emitting diode and determine whether the shape of the measured distribution satisfies the above conditions. In an application using multiple different groups of light emitting diodes, a simplified method may be employed to determine an overall emission energy distribution by measuring an emission energy distribution of a sample light emitting diode selected from each group of light emitting diodes having equal quality, adding a weight to each measured emission energy distribution according to the number of light emitting diodes included in each group and summing up the respective measured emission energy distributions.

The wavelength range in the emission energy distribution herein includes an ultraviolet light region, a visible light region and a near infrared light region. According to this example, it may be determined whether the emission energy distribution satisfies the above conditions, based on at least an energy spectrum of 300 to 830 nm detectable by a general emission spectral measurement device. This is because conventionally-manufactured light emitting diodes for visible light emission generally output 99% or more of emission energy at 300 nm to 830 nm.

The lighting properties of the light emitting diode are affected by the value of drive current and the temperature. The measurement of the emission energy distribution is accordingly performed under the same conditions of drive current and temperature as those adopted during light irradiation for the photochemical reaction. In other words, the measurement of the emission energy distribution is performed under the condition that the drive current applied to the light emitting diode as the subject of measurement of the emission energy distribution is substantially equal to the average value of drive current applied to each light emitting diode during light irradiation for the photochemical reaction. The amount of electric current applied for the photochemical reaction is preferably 0.1% to 100% of the rated current value of the light emitting diode used. The measurement is also performed under the condition that the surface temperature on the rear surface of the light emitting diode is substantially equal to the average temperature of the light emitting diode during light irradiation by the light emitting diode for the photochemical reaction. When a radiator plate, a circuit board with radiator plate, a heat sink or the like is provided on the rear surface of the light emitting diode, the measurement is performed under the temperature condition that the surface temperature of such an element is substantially equal to the average temperature during the photochemical reaction. When the light emitting diode is mounted on, for example, a substrate, the measurement is performed under the temperature condition that the surface temperature of, for example, the substrate is substantially equal to the average temperature during the photochemical reaction.

The material of the radiator plate, the circuit board with radiator plate, the heat sink or the like provided on the rear surface of the light emitting diode may be aluminum or copper having good thermal conductivity. The radiator plate, the circuit board with radiator plate, the heat sink or the like may be provided on the light emitting diode to release heat from the light emitting diode or in some cases to cool down the light emitting diode, to regulate the temperature during the measurement to be substantially equal to the temperature during the photochemical reaction. The light emitting diode generates heat during operation to increase the temperature. The measurement time should thus be set to 10 to 300 ms to keep a temperature rise within 1° C. The temperature during light irradiation for the photochemical reaction should be the average value of the surface temperature of the radiator plate, the circuit board with radiator plate, the heat sink or the like of the light emitting diode.

The emission energy distribution is a distribution obtained by measurement and summation of the outputs in every 5 nm wavelength ranges. When that the more accurate measurement is needed, the emission energy distribution is a distribution obtained by measurement and summation of the outputs preferably in every 0.5 to 1 nm wavelength range. The center value in the wavelength band for the measurement and summation of the outputs should be used for evaluation of the wavelengths, for example, the peak wavelength and the wavelength range (width) outputting the energy having the intensity of or over 5% of Emax. When the measurement is performed prior to the photochemical reaction, the measurement should be performed under the conditions of temperature and drive current expected to be used for the photochemical reaction. According to this example, it is preferable to set the temperature at −20° C. to 50° C. as long as the temperature range does not interfere with the reaction in the liquid. The light emitting diode itself is not exposed to the liquid. The temperature range should thus be set to the range that does not solidify the liquid on the surface irradiated with the light from the light emitting diode. The temperature range is more preferably set at −10° C. to 40° C. This temperature range does not cause evaporation of cyclohexane, one example of a cycloalkane used for production of a cycloalkanone oxime. The lower temperature, however, provides the higher energy conversion efficiency, due to the characteristics of the light emitting diode.

In the light emitting diode used according to this example, the energy conversion efficiency η, i.e., the integrated value of emission energy (effective energy) in the wavelength range of 400 to 760 nm with respect to the input electric power per each light emitting diode, is preferably equal to or higher than 10% or more preferably equal to or higher than 20%. There is no specific limitation on the upper limit of the energy conversion efficiency η. Based on the theoretical upper limit of the external quantum efficiency (ratio of the number of photons taken outside to the number of input electrons), however, the upper limit of the energy conversion efficiency is 75%, for example, at the wavelength of about 400 nm in the above wavelength of 400 to 760 nm. The energy conversion efficiency of 75%, however, has the sufficient advantageous effects, and the energy conversion efficiency of even 60% or lower still has the sufficient advantageous effects by reducing the amount of heat generation compared with an electric discharge lamp. The LED (Luxeon LXML-PL01-0030 manufactured by Philips Lumileds Lighting Company) used in JP '004 has the energy conversion efficiency as low as 7% and does not achieve the efficient reaction result relative to the input electric power.

According to this example, an integrating sphere (PMA-12 manufactured by Hamamatsu Photonics K.K.) is used as the device to measure the emission energy in the wavelength distribution and the energy conversion efficiency η. The integrating sphere allows for measurement of an absolute value of emission energy at each wavelength.

The integrating sphere includes a micro-spectrometer, a high-sensitive multi-channel photo detection element, a current-voltage regulator and a controller. The procedure first detects the photo energy in each wavelength range by the photo detection element, while fixing the value of electric current applied to the light emitting diode to a certain value. The procedure then successively shifts the wavelength range for detection to measure the energy distribution in each wavelength range. On completion of the wavelength shift and the detection with respect to the certain current value, the controller changes the setting to a next current value and repeats the wavelength shift and the detection as described above. The integrating sphere can automatically measure the electric current-wavelength distribution by this procedure. The width of varying the current value (current span), the wavelength range and the width of varying the wavelength (wavelength span) may be changed freely. The measurement of this examination adopts the current span of 100 mA and the wavelength span of 1 nm. These spans are, however, not restrictive but may be changed according to the purpose of the examination.

According to this example, the integrating sphere used has an inner diameter of or over 3 inches (7.6 cm). In the case of difficulty in measurement, however, the integrating sphere used may have an inner diameter of or over 10 inches (25.4 cm). The measurement width at each wavelength is preferably equal to or less than 5 nm and is more preferably in the range of 0.5 to 1 nm. The value determined by measuring the input electric power and dividing the absolute value of the entire emission energy measured by the above measurement procedure by the input electric power is defined as η.

The "selectivity" used according to this example indicates the ratio of the production amount of a cycloalkanone oxime as the target product to the amount of conversion of a cycloalkane containing impurity. "Selectivity" is calculated as the value of the molar amount of production of the cycloalkanone oxime as the numerator relative to the total molar amount of production of the cycloalkanone oxime and impurity generation as the denominator. A selectivity closer to 100% proves that the cycloalkane is used effectively and the target product is obtained efficiently. The analytical values by gas chromatography are used in this measurement procedure.

Figure 2:
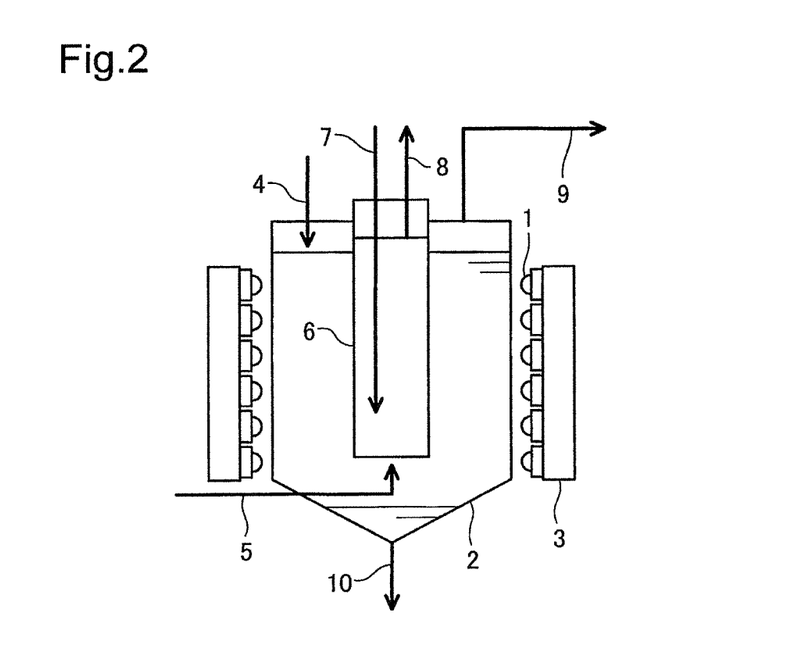
FIG. 2 is a conceptual cross sectional view illustrating one example of a photochemical reaction device using light emitting diodes.

The following describes one example of the photochemical reaction using light emitting diodes with reference to FIG. 2. FIG. 2 is a conceptual cross sectional diagram illustrating one example of a photochemical reaction device using light emitting diodes.

Light emitting diodes 1 used as the light source of this example may be any of a general bombshell type, a surface mount type and a chip type. The light emitting diodes 1 allowing for heat release over the wide area of the rear surface are, however, preferable to reduce a temperature increase of a photoreactive liquid in a photochemical reactor 2 located in the light irradiating direction of the light emitting diodes 1.

Any method may be employed for light irradiation from the light source as long as a photoreactive liquid of a cycloalkane and a photo nitrosating agent or a photoreactive liquid containing their reaction products is effectively irradiated with the light. The method of light irradiation may be, for example, an external irradiation system of irradiating the photoreactive liquid with light from outside of the photochemical reactor 2 as shown in FIG. 2 or an internal irradiation system of directly or indirectly soaking the light source in the photoreactive liquid and irradiating the photoreactive liquid with light from inside of the photochemical reactor 2. Conventional lamps such as electric discharge lamps and fluorescent lamps generally provide the light source in the spherical shape or in the bar-like shape. To ensure the effective use of the light from such a light source, the internal irradiation system is predominant as the conventional light irradiation method. The internal irradiation system has additional advantage that freely changes the distance of irradiating the reaction liquid using one identical light emitter.

The reactor having an array of a large number of small point light sources such as light emitting diodes may, however, be in any shape. The most advantageous shape for the reaction rate and the easiness of installation may be selected as the shape of the reactor. The light emitting diodes 1 are bonded to heat sinks 3 by using a heat conductive adhesive or the like and are arranged to release heat outside of the light emitting diodes 1. A cycloalkane is supplied through a cycloalkane supply line 4 to the photochemical reactor 2 and is discharged with a product of a higher specific gravity through a reaction product line 10. The photo nitrosating agent used in this example is a gaseous agent. The photo nitrosating agent is supplied through a photo nitrosating agent supply line 5 to the photochemical reactor 2 and is discharged through an unreacted gas line 9 after absorption of the photo nitrosating agent into the reaction liquid. The photo nitrosating agent used is the gaseous agent according to this example but may be a liquid agent such as trichloronitrosomethane. The temperature of a reaction tank is controlled by making the flow of cooling water through a reaction cooling water supply line 7 to a cooler 6 and discharging the cooling water after cooling through a reaction cooling water discharge line 8. To keep the temperature of the reaction tank at or over 10° C., it is preferable to use water of or below 10° C. as the coolant.

Figure 4:
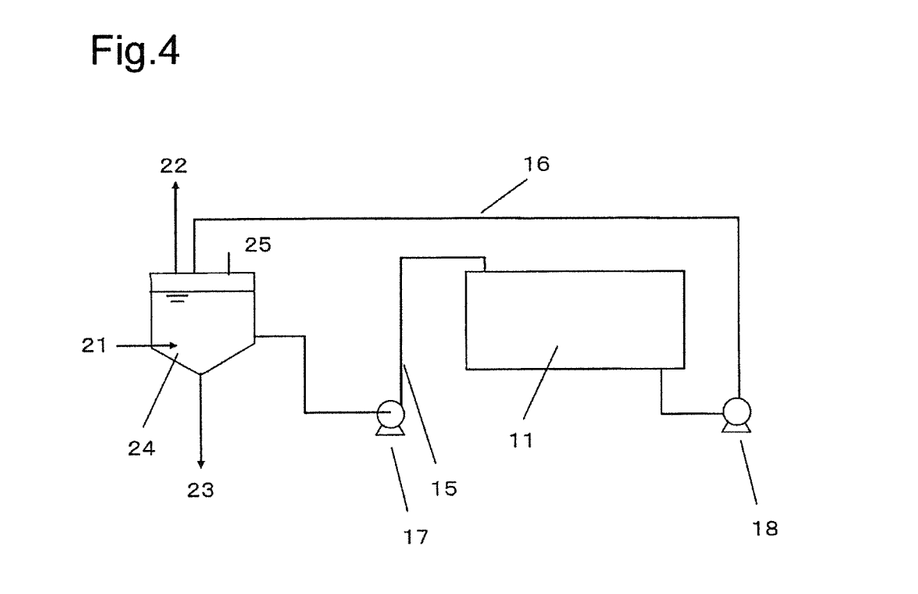
FIG. 4 is a diagram illustrating one example of peripheral equipment of the device used for the photoreaction experiment performed with changing the reaction volume and the amount of irradiation for reaction.

The "reaction volume" herein means the volume of a space where the photochemical reaction of a cycloalkane and a photo nitrosating agent proceeds. The "reaction volume" is the sum of (i) the volume of a portion configured to store a reaction raw material liquid and arranged to include a light irradiation region that is internally irradiated with the light which passes through a wall surface of the reactor made of a transparent material and reaches an obstacle, a wall surface or the like to dissipate; and (ii) the volume of a portion coupled with the above portion (i) to allow for easy replacement of the liquid with the above portion (i). For example, in FIG. 2, there is no exchange of the raw material liquid with the periphery during reaction so that the reaction volume is equal to the overall internal liquid volume of a glass reaction tank included in the photochemical reactor 2. In FIG. 4 described later, on the other hand, the raw reaction liquid is readily exchanged between the liquid volume of a photochemical reactor (variable volume type reactor) 11 and the liquid volume of a separator 24 by a pump during the reaction so that the reaction volume is equal to the total of these liquid volumes. The greater reaction volume is generally thought to be desirable in terms of light absorption, and it is generally thought that the reaction volume is preferably equal to or greater than the distance required for absorption of the entire irradiated light. In the actual state, however, the light absorption proceeds according to Equation (1) below, based on the Lambert-Beer's law on light absorption. The excessive irradiation distance or the excessive reaction volume is accordingly not effective. The higher light absorbance is desirable, but the light absorbance equal to or higher than 50% is preferable from the practical point of view.

$$\text{(Light Absorbance)} = 1 - \exp(-\alpha \times c \times L) \quad (1)$$

where $\alpha$ represents a coefficient, L represents the irradiation distance and c represents the concentration of the nitrosating agent (mol %).

The higher concentration of the photo nitrosating agent is generally thought to be desirable for the greater absorption of the irradiated light. The higher concentration of the photo nitrosating agent is, however, more likely to cause side reactions. This may lead to the phenomenon of increasing the amount of impurity and decreasing the selectivity described later. The excessively low concentration of the photo nitrosating agent, on the other hand, causes insufficient light consumption due to the poor light absorption and is likely to decrease the production amount of a cycloalkanone oxime per unit energy. Based on these phenomena, it is preferable to increase the concentration of the photo nitrosating agent to such an extent that does not increase generation of impurity and thereby to enhance the light absorbance.

Figure 3:
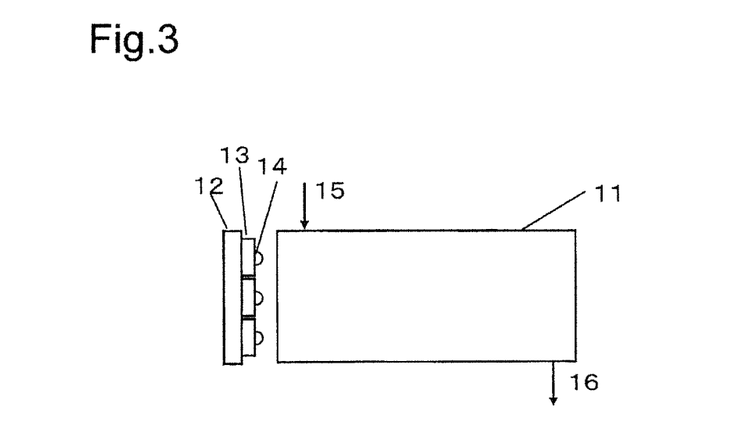
FIG. 3 is a diagram illustrating one example of a device used for a photoreaction experiment performed with changing the reaction volume and the amount of irradiation for reaction.

To further control the setting for the volume of the reactor, one possible measure may adjust and study the reaction volume by providing a reaction device equipped with a photochemical reactor (variable reaction volume type) 11 capable of varying the volume of the reactor as shown in FIG. 3 and changing the length of the photochemical reactor 11 in the light irradiation direction. Such a reaction device may be used for industrial production, although the features of the example are not at all restricted by the shape of this reaction device.

FIG. 3 is a conceptual side view illustrating one example of a reaction device in detail used for a photoreaction experiment performed with changing the reaction volume in examples described later. A plurality of light emitting diode-exposure electrode substrates 13 having light emitting diodes 14 mounted thereon and electrodes for circuit connection exposed outside of the light emitter are placed on the same side relative to a photochemical reactor 11. This structure enables the irradiated light to be introduced into the photochemical reactor 11. The light emitting diodes (light emitting elements) 14 are the very small light sources. Light emitters or modules with arrays of a plurality of light emitting diodes may thus be combined in any arrangement as long as the circuit construction is allowable. As a result, this allows for various arrangements of light irradiation that are not readily achievable by the electric discharge lamp and enables objects in various shapes such as a planar surface and a curved surface, to be irradiated with light. The light-emitting diodes have high directional characteristics so that arraying a plurality of light emitting diodes as a light emitter (module) allows for uniform light emission of the light emitter (module).

The material for the side face of the transparent photochemical reactor 11 may be any material that has the good transmission property of the light emitted from the light emitting diodes used, for example, glass, crystal or a transparent resin such as acrylic resin. A non-light transmission part prohibiting light transmission is preferably covered with, for example, an aluminum foil to prevent dissipation of the irradiated light. When the liquid placed inside the reactor is corrosive, the reactor is preferably made of glass. In an application where the part other than the light transmission part is made of a different material, titanium or tantalum may also be used as the material.

There is no specific limitation on the temperature for emission of the light emitting diodes (light emitting elements) 14. The emission of the light emitting diodes (light emitting elements) 14 is affected by, for example, the ambient temperature such as outside air temperature and the temperatures of the joints of the light emitting diodes, the substrate and the radiator plates. In general, the higher temperature is likely to decrease the emission energy per unit electric power. It is accordingly preferable to suppress a temperature rise of the light emitting diodes. As long as the photonitrosation reaction is allowed, the lower temperature of the light emitting diodes is preferable. One available method of suppressing a temperature rise during emission of the light emitting diodes 14 may be the air-cooling method when the ambient temperature is substantially constant and the air-cooling method can sufficiently prevent heat generation of the light emitting diodes and suppress a temperature rise during emission of the light emitting diodes. For example, a heat sink made of a metal such as aluminum or copper may be provided on the rear surface of light emitting diode-exposure electrode substrates 13 or a circuit base 12 for irradiation of light emitting diodes. To enhance the contact area with the outside air, for example, heat sink fins may be provided to release heat. The cooling method using a coolant may alternatively be adopted for the same purpose. From the practical point of view, the target temperature of the temperature control is preferably equal to or higher than 0° C. Any cooling substance, for example, water, an organic cooling liquid, an inorganic cooling liquid, the air or nitrogen may be used as the coolant. When cyclohexane is used as the raw material, it is preferable to use chilled water of 4° C. to 10° C. according to the relationship to the melting point of cyclohexane.

There is no specific limitation on the number of carbons included in the cycloalkane used according to this example. Preferable examples of the cycloalkane include cyclopropane, cyclobutane, cyclopentane, cyclohexane, cycloheptane, cyclooctane, cyclononane, cyclodecane, cycloundecane and cyclododecane. Especially preferable are cyclohexane as the material of caprolactam and cyclododecane as the material of lauryl lactam.

The cycloalkane may be supplied, for example, through a reactor input material circulation line 15 to the photochemical reactor 11 (FIG. 3). The cycloalkane containing a gaseous photo nitrosating agent injected therein in advance and adjusted to a predetermined concentration may be used as the supply liquid. This allows for supplement of the photo nitrosating agent consumed in the reactor. Alternatively, the reaction may be performed, with continuously injecting the photo nitrosating agent into the supply liquid. In the latter case, a preferable procedure may control the injection amount of the photo nitrosating agent with monitoring the concentration of the photo nitrosating agent in the reaction liquid.

Nitrosyl chloride or trichloronitrosomethane may be used as the photo nitrosating agent. Another available method may use a gas producing the photo nitrosating agent through a reaction. For example, any of a mixed gas of nitrosyl chloride and hydrogen chloride, a mixed gas of nitrogen monoxide and chlorine, a mixed gas of nitrogen monoxide, chlorine and hydrogen chloride and a mixed gas of dinitrogen trioxide ($N_2O_3$) gas and chlorine may act as nitrosyl chloride by a reaction in the photoreaction system. The supply mode of the nitrosating agent is accordingly not limited. Trichloronitrosomethane obtained by the photoreaction of nitrosyl chloride and chloroform may also be used as the photo nitrosating agent. The concentration of the photo nitrosating agent may be measured with regard to a sampled liquid by iodine color change and titration with sodium thiosulfate as described later or may be determined by a simplified method using a light transmission rate. The concentration of the photo nitrosating agent may be adjusted by regulating the amount of nitrosyl chloride in the reaction liquid.

The photochemical reaction of the cycloalkane and the photo nitrosating agent by light irradiation from the light emitting diodes results in yielding a cycloalkanone oxime corresponding to the number of carbons included in the cycloalkane.

The photochemical reaction in the presence of hydrogen chloride gives the cycloalkanone oxime in the form of a hydrochloride of cycloalkanone oxime. The cycloalkanone oxime may be kept in the hydrochloride form. For example, the photonitrosation reaction of cyclohexane using nitrosyl chloride gives cyclohexanone oxime. The resulting cyclohexanone oxime obtained by the reaction sediments in the tank of the photochemical reactor 11 to be accumulated as the oily product. This oily product is extracted via a reaction liquid circulation line 16 (FIG. 3). The unreacted liquid is discharged with the oily product via the unreacted cyclohexane+cyclohexanone oxime circulation line 16 and is separated from the oily product outside of the system by the specific gravity difference. In many cases, the unreacted substance is then re-supplied as the raw material to the photoreaction tank.

FIG. 4 illustrates one example of peripheral equipment of the device of FIG. 3 used for the photoreaction experiment. Unreacted cyclohexane as the unreacted material and cyclohexanone oxime as the oily product are introduced from the photochemical reactor 11 through the reaction liquid circulation line 16 to a separator 24 and are discharged by using a reaction liquid circulation line pump 18. Cyclohexane is separated from the oily product in the separator 24 by the specific gravity difference and is supplied back through the reactor input material circulation line 15 to the photochemical reactor 11 by using a reactor input material circulation line pump 17. In the separator 24, nitrosyl chloride is injected through a nitrosyl chloride injection line 21 and may be absorbed by cyclohexane. The unreacted gas is discharged through a nitrosyl chloride-unreacted gas discharge line 22. Cyclohexanone oxime as the product is extracted through an oily product extraction line 23. An amount of cyclohexane corresponding to its reduction by extraction of the product may be supplied through a raw material supply line 25.

According to another example, the photochemical reaction may be performed using a device having a cylindrical light emitter assembly (i.e., light emitter module) with a large number of light emitting diodes bonded outward on one single cylinder located in a reactor. In this case, the reaction volume, i.e., the distance by which the light passes through a reaction liquid in the course of light irradiation may be adjusted by regulating the diameter of an outer cylinder of the reactor. In another example, the reaction volume may be adjusted by placing a baffle plate or a cooling plate in the irradiation direction to appropriately interfere with light irradiation. In an application using a plurality of light emitter modules for the reaction, the reaction volume may be adjusted by regulating the distance between the light emitter modules to an optimum value, in addition to regulating the diameter of the outer cylinder or placing the baffle plate or the cooling plate. Strictly speaking, there is a clearance between adjacent light emitter modules, but the light leaking through this clearance has only a limited influence. There is no specific limitation on the arrangement of a plurality of light emitter modules in the horizontal plane. The triangular arrangement of placing the respective light emitter modules at the positions corresponding to apexes of an equilateral triangle equalizes the distances between the respective light emitters and enables a greater number of light emitters to be placed in a limited area.

EXAMPLES

An example of our method is described below.

The following describes the conditions of the basic operation for production of a cycloalkanone oxime in Examples and Comparative Examples. Cycloalkanone oximes were produced by changing part of these conditions to conditions specified in the respective Examples and Comparative Examples.

A photochemical reaction device similar to the device shown in FIGS. 3 and 4 was used for the photoreaction test. Four different "Pyrex (registered trademark)" glass cylinders commonly having the inner bore of 10 cm and differently having the lengths of 4.5 cm, 9 cm, 22.5 cm and 45 cm were used as the cylindrical photochemical reactor 11. Photoreaction tanks were successively replaced according to the reaction volumes set as the experimental condition, and data at the respective reaction volumes were measured. The light emitting diode-exposure electrode substrates 13, the circuit base 12 for irradiation of light emitting diodes and the light emitting diodes (light emitting elements) 14 working as the light source were provided as a commercially available integral product. The light emitting diodes 14 used were light emitting diodes with the maximum energy peak at the wavelength of 615 nm (light emitting diodes Red Orange XPERDO-L1-0000-00701 or XPERDO-1L-0000-00801 manufactured by Cree, Inc. or light emitting diodes LXML-PH01-0050 manufactured by Philips Lumileds Lighting Company) mounted on an aluminum circular substrate (TR-RE90 φ75 manufactured by EFFECT Corporation) as the circuit base 12 for irradiation of light emitting diodes. All the light emitting diode-exposure electrode substrates 13 and all the light emitting diodes 14 used were respectively the products from the same lots. A light emitter module was assembled by arranging ninety light-emitting diode-exposure electrode substrates 13 respectively having light emitting diodes 14 in a rectangular arrangement on a circular plate of 7.5 cmφ. An aluminum heat sink for cooling was attached to the light emitter module on the side opposite to the side on which the light emitting diode-exposure electrode substrates 13 were placed. The light irradiation planes of the respective light emitting diodes 14 were arranged outside of and opposed to one of the end faces (circular shape) of the cylindrical form of the photochemical reactor (variable irradiation distance type) 11. The heat sink was indirectly cooled down by the external flow of water. The temperature of the cooling water was set to 10° C.

A method of irradiating the photoreaction liquid from outside of the photochemical reactor 11 through an outer glass wall of the end faces (circular shape) of the cylindrical form of the photochemical reactor 11 was adopted for the system of light irradiation with light emitting diodes. A set of DC power supply unit was used for light emission, in which 30 light emitting diodes were connected in series in each line and a total of three lines were connected in parallel. The average drive current per each light emitting diode was 0.35 to 0.45 A/diode, and the total electric power input into all the light emitting diodes was 65 to 85 W.

The procedure supplied cyclohexane (special grade chemical, manufactured by Katayama Chemical Industries Co., Ltd.) through the raw material supply line 25 to the photochemical reactor 11 and the separator 24 with adequately changing the supply amount as shown in Table 1 and kept the reaction temperature at 20° C. The procedure also supplied and continuously injected hydrogen chloride gas (manufactured by Tsurumi Soda Co., Ltd.) at the flow rate of 2000 ml/min and nitrosyl chloride gas (obtained by synthetic reaction of nitrosylsulfuric acid and hydrogen chloride and subsequent distillation and purification) at the flow rate of 50 to 300 ml/min through the nitrosyl chloride injection line 21 into the lower part of the separator 24. The hydrogen chloride gas and the nitrosyl chloride gas were then circulated at the rate of 10 ml/min between the photochemical reactor 11 and the separator 24. This caused cyclohexane to be exposed to the nitrosyl chloride gas in the separator 24 and subsequently fed to the photochemical reactor 11 through the reactor input material circulation line 15. The concentration of nitrosyl chloride was measured by the following method. Samples of the reaction liquid were extracted from the separator 24 at the intervals of every 30 minutes after the start of the injection. Each of the samples was dispersed in a methanol solution of potassium iodide to produce iodine, and the dispersion was then subject to oxidation-reduction titration using an aqueous solution of sodium thiosulfate.

When the reaction started, the reaction product was accumulated in the form of oily product on the bottom of the photochemical reactor 11. The oily product on the bottom was extracted with the unreacted material through the reaction liquid circulation line 16 by the reaction liquid circulation line pump 18 shown in FIG. 4 while being protected from direct light irradiation, and was then separated in the separator 24 by the specific gravity difference. The separated oily product was extracted through the oily product extraction line 23 at regular intervals. After the test, the total mass of the extracted oily product was measured.

The temperature of the photoreaction liquid was determined by measuring the temperature of the liquid extracted from the photochemical reactor 11 through the reaction liquid circulation line 16 by the pump. In an application using an electric discharge lamp, it is required to cool down the light irradiation plane due to the heat generated by the electric discharge lamp. The light emitting diodes 1, however, have extremely low heat generation on the light irradiation plane and accordingly do not need to cool down the light irradiation plane.

The light emitting diodes 14 were lit up to start the reaction. After the reaction liquid was fed to the separator 24, only the oily product was accumulated in the separator 24 due to the specific gravity difference, while unreacted cyclohexane was exposed to nitrosyl chloride and was re-supplied to the photochemical reactor 11.

The exhaust gas was discharged through the nitrosyl chloride-unreacted gas discharge line 22 and was absorbed into water in a scrubber. The absorbed liquid was neutralized with soda ash.

For the purpose of stable measurement, the subject of evaluation was the oily product extracted after elapse of 120 minutes to 180 minutes since the start of lighting of the light emitting diodes.

The amounts of cyclohexanone oxime and the impurity were measured by GC analysis (GC-14B manufactured by Shimadzu Corporation) after the extracted oily product was dissolved in an ethanol solution and was neutralized with sodium bicarbonate powder. The concentration (mass %) of cyclohexanone oxime was determined from the calibration curve of GC analysis. The production amount (g) of cyclohexanone oxime obtained by the reaction was calculated from the mass (g) of the oily product and was subject to mole conversion as appropriate. The conditions of GC analysis were as follows: 7% Thermon-3000 used as the stationary phase liquid; 80 to 100 meshes of Chromosorb W-AW (DMCS) used as the stationary phase carrier; glass column of 2.1 m in length and 3.2 mm in inner bore; nitrogen gas at the rate of 25 ml/minute used as the carrier gas; temperature of the column thermostat at 180° C. and temperature of the inlet at 240° C.; FID (hydrogen flame ionization detector) used as the detector; and diphenyl ether used as the internal standard material.

The yield (g/kWh) of cyclohexanone oxime was calculated as the amount (g) of cyclohexanone oxime produced relative to the input power (kWh) per hour.

Example 1

The reaction was performed using a photochemical reactor having the length, i.e., the irradiation distance of light, of 4.5 cm with a supply of 2 liters of cyclohexane and using light emitting diodes Red Orange XPERDO-L1-0000-00701 manufactured by Cree, Inc. (energy conversion efficiency of 35%) as the light emitting diodes for light irradiation (the same applied to Examples 2 to 4). The light emitting diodes Red Orange XPERDO-L1-0000-00701 manufactured by Cree, Inc. are designed to emit light satisfying the conditions that, in an emission energy distribution with respect to the wavelength of light, the wavelength providing the maximum value of emission energy is 600 nm to 650 nm and a continuous wavelength range including the wavelength providing the maximum value and outputting energy of or over 5% of the maximum value is equal to or less than 150 nm. Under adjustment of the amount of nitrosyl chloride injected into a separator, the concentration of nitrosyl chloride in the reaction liquid after 120 minutes to after 180 minutes was measured to be 0.4 mol %. The other conditions were the same as those of the basic operation described above and those specified in Table 1. The results are shown in Table 1.

Example 2

The reaction was performed using a photochemical reactor having the irradiation distance of light, i.e., the cylinder length, of 9 cm. The supply volume of cyclohexane was 2.3 liters. Under adjustment of the amount of nitrosyl chloride injected into a separator, the concentration of nitrosyl chloride in the reaction liquid after 120 minutes to after 180 minutes was measured to be 0.4 mol %. The other conditions were the same as those of Example 1. The results are shown in Table 1.

Example 3

The reaction was performed using a photochemical reactor having the irradiation distance of light, i.e., the cylinder length, of 22.5 cm. The supply volume of cyclohexane was 3.2 liters. Under adjustment of the amount of nitrosyl chloride injected into a separator, the concentration of nitrosyl chloride in the reaction liquid after 120 minutes to after 180 minutes was measured to be 0.4 mol %. The other conditions were the same as those of Example 1. The results are shown in Table 1.

Example 4

The reaction was performed using a photochemical reactor having the irradiation distance of light, i.e., the cylinder length, of 45 cm. The supply volume of cyclohexane was 5.4 liters. Under adjustment of the amount of nitrosyl chloride injected into a separator, the concentration of nitrosyl chloride in the reaction liquid after 120 minutes to after 180 minutes was measured to be 0.4 mol %. The other conditions were the same as those of Example 1. The results are shown in Table 1.

Example 5

The reaction was performed using XPERDO-L1-0000-00801 of the higher performance manufactured by Cree, Inc. than that of XPERDO-L1-0000-00701 used in Examples 2 to 4 as light emitting diodes and using a photochemical reactor having the irradiation distance of light, i.e., the cylinder length, of 9 cm. The light emitting diodes Red Orange XPERDO-L1-0000-00801 manufactured by Cree, Inc. are designed to emit light satisfying the conditions that, in the emission energy distribution with respect to the wavelength of light, the wavelength providing the maximum value of emission energy is 600 nm to 650 nm and the continuous wavelength range including the wavelength providing the maximum value and outputting energy of or over 5% of the maximum value is equal to or less than 150 nm. The supply volume of cyclohexane was 2.3 liters. Under adjustment of the amount of nitrosyl chloride injected into a separator, the concentration of nitrosyl chloride in the reaction liquid after 120 minutes to after 180 minutes was measured to be 0.4 mol %. The other conditions were the same as those of Example 1. The results are shown in Table 1.

Comparative Example 1

The reaction was performed using a photochemical reactor having the irradiation distance of light, i.e., the cylinder length, of 22.5 cm and using light emitting diodes Red Orange LXML-PH01-0050 manufactured by Philips Lumileds Lighting Company (energy conversion efficiency of 20%) as the light emitting diodes for light irradiation. The light emitting diodes Red Orange LXML-PH01-0050 manufactured by Philips Lumileds Lighting Company are designed to emit light which does not satisfy the following conditions: in the emission energy distribution with respect to the wavelength of light, (i) the wavelength providing the maximum value of emission energy is 600 nm to 650 nm; and (ii) the continuous wavelength range including the wavelength providing the maximum value and outputting energy of or over 5% of the maximum value is equal to or less than 150 nm. Under adjustment of the amount of nitrosyl chloride injected into a separator, the concentration of nitrosyl chloride in the reaction liquid after 120 minutes to after 180 minutes was measured to be 0.3 mol %. The other conditions were the same as those of the basic operation described above and those specified in Table 1. The results are shown in Table 1.

Comparative Example 2

The reaction was performed using a photochemical reactor having the irradiation distance of light, i.e., the cylinder length, of 45 cm. Under adjustment of the amount of nitrosyl chloride injected into a separator, the concentration of nitrosyl chloride in the reaction liquid after 120 minutes to after 180 minutes was measured to be 0.3 mol %. The other conditions were the same as those of the basic operation described above and those specified in Table 1. The results are shown in Table 1.

Comparative Example 3

The reaction was performed using a photochemical reactor having the irradiation distance of light, i.e., the cylinder length, of 22.5 cm and changing the light emitting diodes for light irradiation to light emitting diodes Red Orange XPERDO-L1-0000-00701 manufactured by Cree, Inc. (energy conversion efficiency of 35%). Under adjustment of the amount of nitrosyl chloride injected into a separator, the concentration of nitrosyl chloride in the reaction liquid after 120 minutes to after 180 minutes was measured to be 0.4 mol %. The other conditions were the same as those of the basic operation described above and those specified in Table 1. The results are shown in Table 1.

Comparative Example 4

The reaction was performed using a photochemical reactor having the irradiation distance of light, i.e., the cylinder length, of 45 cm. Under adjustment of the amount of nitrosyl chloride injected into a separator, the concentration of nitrosyl chloride in the reaction liquid after 120 minutes to after 180 minutes was measured to be 0.4 mol %. The other conditions were the same as those of the basic operation described above and those specified in Table 1. The results are shown in Table 1.

TABLE 1

| | | | Liquid Volume V L | Electric Power E w | Energy Conversion Efficiency η % | ηE/V W/L | Irradiation Distance mm | Electric Current A/Diode | NOCl in Liquid mol % | Yield of Oxime g/kwh | Selection Rate % |
|---|---|---|---|---|---|---|---|---|---|---|---|
| EX 1 | CREE | XPRDO-L1-0000-00701 | 2 | 65 | 35 | 11.4 | 45 | 0.35 | 0.4 | 222.9 | 86.8 |
| Ex 2 | CREE | XPRDO-L1-0000-00701 | 2.3 | 65 | 35 | 9.9 | 90 | 0.35 | 0.4 | 348.8 | 86.4 |
| EX 3 | CREE | XPRDO-L1-0000-00701 | 3.2 | 65 | 35 | 7.1 | 225 | 0.35 | 0.4 | 404.4 | 85.1 |
| EX 4 | CREE | XPRDO-L1-0000-00701 | 5.4 | 85 | 35 | 5.5 | 450 | | 0.4 | 406.2 | 87.6 |
| EX 5 | CREE | XPRDO-L1-0000-00801 | 2.3 | 74.5 | 38 | 12.3 | 90 | 0.35 | 0.4 | 397.9 | 87.7 |
| COMP EX 1 | Lumileds | LXML-PH01-0050 | 6 | 85 | 20 | 2.8 | 225 | 0.35 | 0.3 | 140 | 80.8 |
| COMP EX 2 | Lumileds | LXML-PH01-0050 | 6 | 85 | 20 | 2.8 | 450 | 0.35 | 0.3 | 153 | 79.0 |
| COMP EX 3 | CREE | XPRDO-L1-0000-00701 | 6 | 85 | 35 | 5.0 | 225 | 0.35 | 0.4 | 460 | 82.8 |
| COMP EX 4 | CREE | XPRDO-L1-0000-00701 | 6 | 85 | 35 | 5.0 | 450 | 0.35 | 0.4 | 419 | 79.2 |

Examples 1 to 4 provided the high efficiencies as the selectivity of 85.1% to 87.6% at the amount of energy irradiation per unit volume ηE/V equal to or greater than 5.5 W/L, irrespective of the irradiation distance. These Examples also kept the high yields of oxime.

Comparative Examples 1 to 4 had the decreased efficiencies as the selectivity of 79.0% to 82.8% with changing the irradiation distance from 22.5 cm to 45 cm. The Comparative Examples provided substantially equivalent yields of oxime under the condition of the same energy conversion efficiency.

The results prove improvement of the selectivity while keeping the yield of oxime when the amount of energy irradiation per unit volume ηE/V is equal to or greater than 5.5 W/L.

The foregoing describes our methods in detail with reference to some preferable examples. The methods are, however, not limited to any of the examples and the configurations described above. The methods include a variety of modifications and equivalent configurations. Additionally, the respective components are described in various combinations and configurations. These are, however, only illustrative. The number of each of these components may be increased or may be decreased, and may be even only one. All of such modifications should be construed to be within the scope of this disclosure.

INDUSTRIAL APPLICABILITY

Light emitting diodes have little effect on the global environment, allow for the efficient use of energy and have the long life so that the photochemical reaction or more specifically photonitrosation reaction is enabled by using the light emitting diodes expected to be the light source for the next generation, as the light source. As a result, the applicability of the light emitting diodes to the photochemical reaction expands the use of the light emitting diodes. Additionally, application of light emitting diodes to production taking advantage of the photochemical reaction (for example, production of caprolactam or lauryl lactam or more specifically production of caprolactam from cyclohexanone oxime by the photonitrosation reaction, although the range of application of our methods is not limited to such production) enables the emission energy to be efficiently utilized for the photonitrosation reaction and allows for reduction of the environment load, energy saving and life extension while being expected to have significant cost reduction.

The invention claimed is:

1. A method of producing a cycloalkanone oxime by a photochemical reaction of a cycloalkane with a photo nitrosating agent in a liquid by light irradiation comprising:
   irradiating the liquid with a light emitting diode configured to emit light satisfying conditions that, in an emission energy distribution with respect to wavelength of light, a wavelength providing a maximum value of emission energy is 600 nm to 650 nm and a continuous wavelength range including the wavelength providing the maximum value and outputting energy of or over 5% of the maximum value is equal to or less than 150 nm, wherein
   a ratio $\eta E/V$ of a light irradiation energy $\eta E$ out of electric power E input into the light emitting diode to a reaction volume V which is a volume of a space for the photochemical reaction of the cycloalkane with the photo nitrosating agent is equal to or greater than 5.5 w/L and equal to or less than 15.0 w/L,
   the selectivity calculated as a value of a molar amount of production of the cycloalkanone oxime as a numerator relative to a total molar amount of production of the cycloalkanone oxime and impurity generation as a denominator is equal to or greater than 85.1%, wherein
   an energy conversion efficiency of the light emitting diode is equal to or higher than 10%, the energy conversion efficiency being an integrated value of emission energy (effective energy) in the wavelength range of 400 to 760 nm with respect to the input electric power per each light emitting diode.

2. The method according to claim 1,
   wherein the cycloalkane is cyclohexane or cyclododecane, and
   the cycloalkanone oxime is cyclohexanone oxime or cyclododecanone oxime.

3. A method of producing a lactam comprising reacting the cycloalkanone oxime produced by the method according to claim 1.

4. A method of increasing selectivity of a cycloalkanone oxime by a photochemical reaction of a cycloalkane with a photo nitrosating agent in a liquid by light irradiation comprising:
   irradiating the liquid with a light emitting diode configured to emit light satisfying conditions that, in an emission energy distribution with respect to wavelength of light, a wavelength providing a maximum value of emission energy is 600 nm to 650 nm and a continuous wavelength range including the wavelength providing the maximum value and outputting energy of or over 5% of the maximum value is equal to or less than 150 nm, wherein a ratio $\eta E/V$ of a light irradiation energy $\eta E$ out of electric power E input into the light emitting diode to a reaction volume V which is a volume of a space for the photochemical reaction of the cycloalkane with the photo nitrosating agent is equal to or greater than 5.5 w/L and equal to or less than 15.0 w/L, wherein
   the selectivity is calculated as a value of a molar amount of production of the cycloalkanone oxime as a numerator relative to a total molar amount of production of the cycloalkanone oxime and impurity generation as a denominator, wherein
   an energy conversion efficiency of the light emitting diode is equal to or higher than 10%, the energy conversion efficiency being an integrated value of emission energy (effective energy) in the wavelength range of 400 to 760 nm with respect to the input electric power per each light emitting diode.

* * * * *